United States Patent
Endo et al.

(10) Patent No.: US 10,074,174 B2
(45) Date of Patent: Sep. 11, 2018

(54) IMAGE PROCESSING APPARATUS THAT SETS IMAGING REGION OF OBJECT BEFORE IMAGING THE OBJECT

(71) Applicant: CANON KABUSHIKI KAISHA, Tokyo (JP)

(72) Inventors: Takaaki Endo, Urayasu (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 13 days.

(21) Appl. No.: 15/103,385

(22) PCT Filed: Jan. 8, 2015

(86) PCT No.: PCT/JP2015/050996
§ 371 (c)(1),
(2) Date: Jun. 10, 2016

(87) PCT Pub. No.: WO2015/108128
PCT Pub. Date: Jul. 23, 2015

(65) Prior Publication Data
US 2016/0314582 A1    Oct. 27, 2016

(30) Foreign Application Priority Data

Jan. 16, 2014 (JP) ................. 2014-006215
Nov. 12, 2014 (JP) ................. 2014-230105

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0035* (2013.01); *A61B 5/0037* (2013.01);
(Continued)

(58) Field of Classification Search
CPC ......... G06T 7/0014; G06T 2207/10088; G06T 7/0012; G06T 2207/30068; G06T 2210/41;
(Continued)

(56) References Cited

U.S. PATENT DOCUMENTS 9,123,096 B2    9/2015  Miyasa et al. ................. 382/131
2008/0292164 A1*  11/2008  Azar ..................... A61B 5/0091
382/131
(Continued)

FOREIGN PATENT DOCUMENTS

CN    101511273 A    8/2009
CN    102727258 A    10/2012
(Continued)

OTHER PUBLICATIONS

ESR dated Jul. 24, 2017 in Eur. Pat. App. 14878958.9 (in English).
(Continued)

*Primary Examiner* — Vu Le
*Assistant Examiner* — Guillermo Rivera-Martinez
(74) *Attorney, Agent, or Firm* — Fitzpatrick Cella Harper and Scinto

(57) ABSTRACT

An image processing apparatus comprising: first image obtaining means for obtaining a first image of an object in a first shape state; imaging region setting means for setting an imaging region of the object in a second shape state; deformation information obtaining means for obtaining deformation information indicating deformation of the object from the second shape state to the first shape state; corresponding region calculating means for calculating a corresponding region that corresponds to the imaging region in the first shape state based on the deformation information; and display image generating means for generating a display image based on the first image and the corresponding region.

14 Claims, 11 Drawing Sheets

(51) Int. Cl.
*A61B 5/055* (2006.01)
*A61B 5/00* (2006.01)
*G06T 7/30* (2017.01)

(52) U.S. Cl.
CPC .......... *A61B 5/0091* (2013.01); *A61B 5/0095* (2013.01); *A61B 5/055* (2013.01); *A61B 5/4312* (2013.01); *G06T 7/30* (2017.01); *A61B 2576/02* (2013.01); *G06T 2207/10088* (2013.01); *G06T 2207/10132* (2013.01); *G06T 2207/20021* (2013.01); *G06T 2207/30068* (2013.01); *G06T 2207/30168* (2013.01)

(58) Field of Classification Search
CPC .......... G06T 3/0093; G06T 2219/2021; G06T 19/00; A61B 5/0091; G06K 2209/057
See application file for complete search history.

(56) References Cited

U.S. PATENT DOCUMENTS

| | | |
|---|---|---|
| 2009/0264758 A1 | 10/2009 | Fujita et al. |
| 2010/0087733 A1 | 4/2010 | Nakajima et al. ............. 600/437 |
| 2010/0284591 A1* | 11/2010 | Arnon .................... A61B 5/015 382/128 |
| 2011/0199390 A1 | 8/2011 | Iizuka et al. .................. 345/629 |
| 2011/0210261 A1* | 9/2011 | Maurer, Jr. .............. A61N 5/10 250/393 |
| 2011/0216958 A1 | 9/2011 | Satoh et al. .................. 382/131 |
| 2011/0262015 A1* | 10/2011 | Ishikawa .............. G06K 9/6206 382/128 |
| 2012/0114213 A1* | 5/2012 | Buelow ................. G06T 7/0032 382/131 |
| 2012/0253173 A1 | 10/2012 | Endo et al. |
| 2012/0262460 A1 | 10/2012 | Endo et al. .................... 345/441 |
| 2012/0321161 A1 | 12/2012 | Ishikawa et al. ............. 382/131 |
| 2013/0051646 A1 | 2/2013 | Nakano et al. ............. 382/131 |
| 2013/0165765 A1 | 6/2013 | Nishihara ..................... 600/407 |
| 2013/0182901 A1 | 7/2013 | Ishida et al. .................. 382/103 |
| 2013/0188851 A1 | 7/2013 | Miyasa et al. ................ 382/131 |
| 2013/0267856 A1 | 10/2013 | Watanabe et al. ............. 600/476 |
| 2014/0037168 A1 | 2/2014 | Ishikawa et al. ............. 382/130 |
| 2016/0228075 A1* | 8/2016 | Kitamura ................. A61B 6/12 |

FOREIGN PATENT DOCUMENTS

| | | |
|---|---|---|
| EP | 2064996 | 6/2009 |
| JP | 2007-029353 | 2/2007 |
| JP | 2010-088627 | 4/2010 |
| JP | 2012-217769 | 11/2012 |
| JP | 2013-059658 | 4/2013 |
| WO | 2013/076616 A1 | 5/2013 |

OTHER PUBLICATIONS

EESR dated Aug. 10, 2017, in counterpart European Patent Application 15737331.7 (in English).
Y. Hu et al., "A Statistical Motion Model Based on Biomechanical Simulations", *Proc. MICCAI 2008, Part I*, LNCS 5241, pp. 737-744 (2008).
C. Tanner et al., "Breast Shapes on Real and Simulated Mammograms", *Proc. Int. Workshop on Digital Mammography 2010* (IWDM 2010), LNCS 6136, pp. 540-547 (2010).
A.W.C. Lee et al., "Breast X-Ray and MR Image Fusion Using Finite Element Modeling", *Proc. Workshop on Breast Image Analysis in conjunction with MICCAI 2011*, pp. 129-136 (2011).
U.S. Appl. No. 15/103,464, filed Jun. 10, 2016.
U.S. Appl. No. 15/103,519, filed Jun. 10, 2016.

* cited by examiner

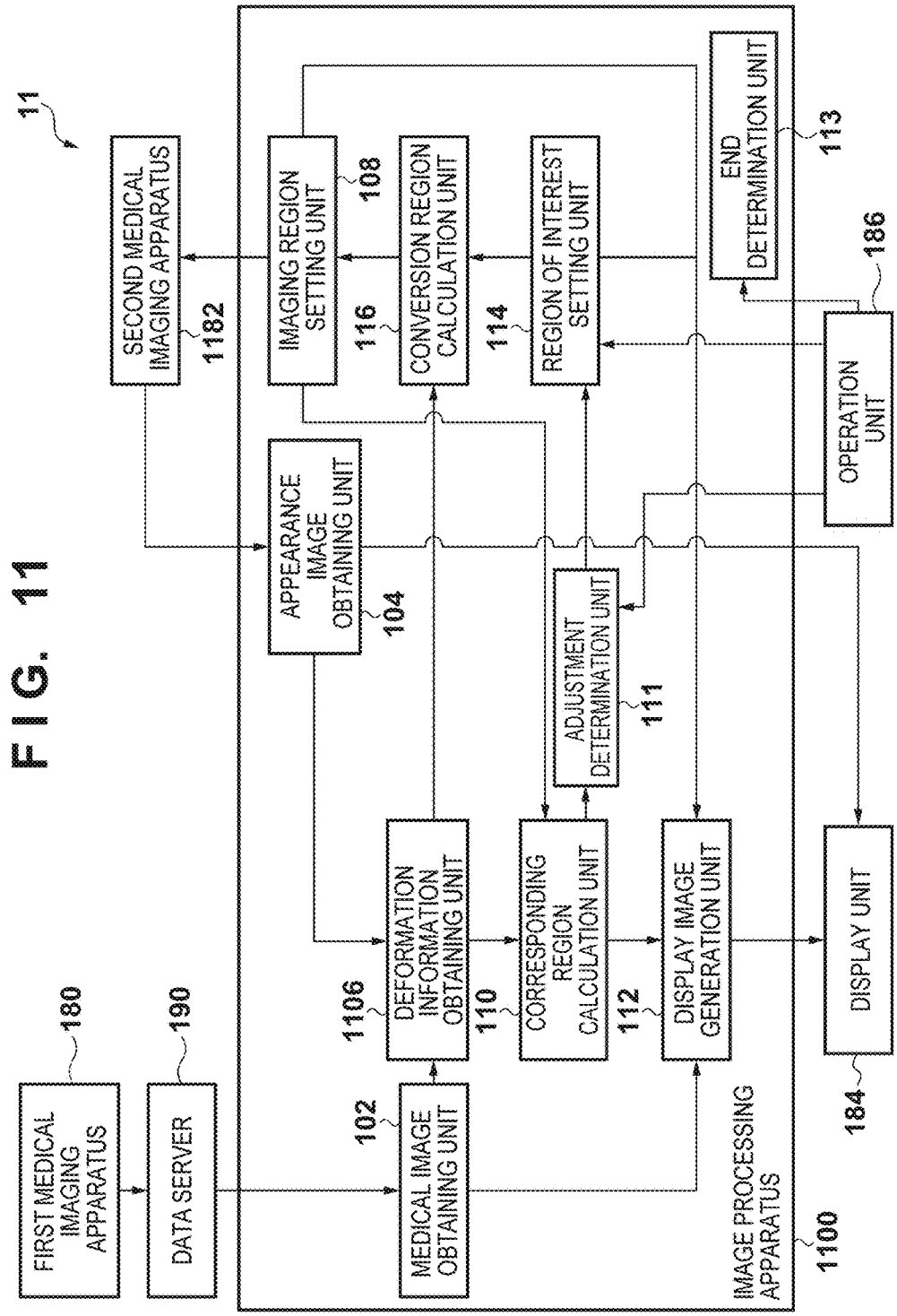

IMAGE PROCESSING APPARATUS THAT SETS IMAGING REGION OF OBJECT BEFORE IMAGING THE OBJECT

TECHNICAL FIELD

The present invention relates to an image processing apparatus, a control method for an image processing apparatus, and a storage medium, and in particular to a technique to process medical images captured by various types of medical image acquisition apparatuses (modalities).

BACKGROUND ART

In recent years, photoacoustic tomography (PAT) imaging apparatuses (PAT apparatuses) have been developed in the medical field. PAT apparatuses excite absorbing materials inside an object by irradiating the object with optical pulses, and detect photoacoustic signals generated by thermoelastic expansion of the absorbing materials, so as to form images of properties of the object related to optical absorption. That is to say, images of an optical energy deposition amount distribution (optical energy absorption density distribution) inside the object with respect to irradiation light are formed. Also, based on this, images of an optical absorption coefficient distribution in the object related to an irradiation wavelength are formed. Furthermore, based on optical absorption coefficient distributions related to a plurality of wavelengths, images of the states of materials constructing the object (e.g., oxygen saturation of hemoglobin) can also be formed. These images are expected to visualize information related to new blood vessels generated inside and outside a tumor, such as cancer. Hereinafter, these images are collectively referred to as photoacoustic tomography images (PAT images).

With PAT apparatuses, irradiation is performed with near infrared ray pulses with a small energy, and therefore it is difficult to form images of deep parts of an object compared to the case of X-rays and like. In view of this, in Japanese Patent Laid-Open No. 2010-88627, imaging is performed in a state where a breast is held by two flat plates (hereinafter referred to as holding plates) and reduced in thickness in one form of a PAT apparatus using the breast as an object. At this time, an irradiation range of the near infrared ray pulses (hereinafter referred to as an imaging region) is set two-dimensionally on a planar surface of a holding plate that holds the breast.

Japanese Patent Laid-Open No. 2007-29353 discloses a technique to display an X-ray irradiation field and an X-ray detection field as visually distinguishable pictures in such a manner that they are overlapped over an appearance image obtained by imaging a body surface of an object with a camera.

However, the techniques of Japanese Patent Laid-Open No. 2010-88627 and Japanese Patent Laid-Open No. 2007-29353 are problematic in that, in a case where a region of attention in the object is not on the body surface but is inside the body of the object, an accurate range of the region of attention is unknown, and therefore it is difficult to appropriately set an imaging region.

In view of the above problem, the present invention provides a technique to set an imaging region such that a region of attention inside an object is imaged appropriately.

SUMMARY OF INVENTION

According to one aspect of the present invention, there is provided an image processing apparatus comprising: first image obtaining means for obtaining a first image of an object in a first shape state; imaging region setting means for setting an imaging region of the object in a second shape state; deformation information obtaining means for obtaining deformation information indicating deformation of the object from the second shape state to the first shape state; corresponding region calculating means for calculating a corresponding region that corresponds to the imaging region in the first shape state based on the deformation information; and display image generating means for generating a display image based on the first image and the corresponding region.

Further features of the present invention will become apparent from the following description of exemplary embodiments (with reference to the attached drawings).

BRIEF DESCRIPTION OF DRAWINGS

FIG. 11 shows functional configurations of an image diagnostic system and an image processing apparatus according to a third embodiment.

DESCRIPTION OF EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

An image processing apparatus according to the present embodiment enables confirmation and adjustment of an imaging region by converting an imaging region of a photoacoustic tomography image (PAT image) into a corresponding region in a pre-deformation MRI (magnetic resonance imaging) image and displaying the corresponding region based on the result of estimation of deformation at the time of holding a breast serving as an object with two flat plates (holding plates). It is assumed that an imaging region according to the present embodiment denotes a candidate region that serves as an index at the time of capturing a PAT image. An actual range for capturing a PAT image (an irradiation range of near infrared ray pulses) may be set separately with reference to the imaging region. The following describes an image diagnostic system according to the present embodiment and an image processing apparatus included in this image diagnostic system.

<Configuration of Image Diagnostic System 1>

Figure 1:
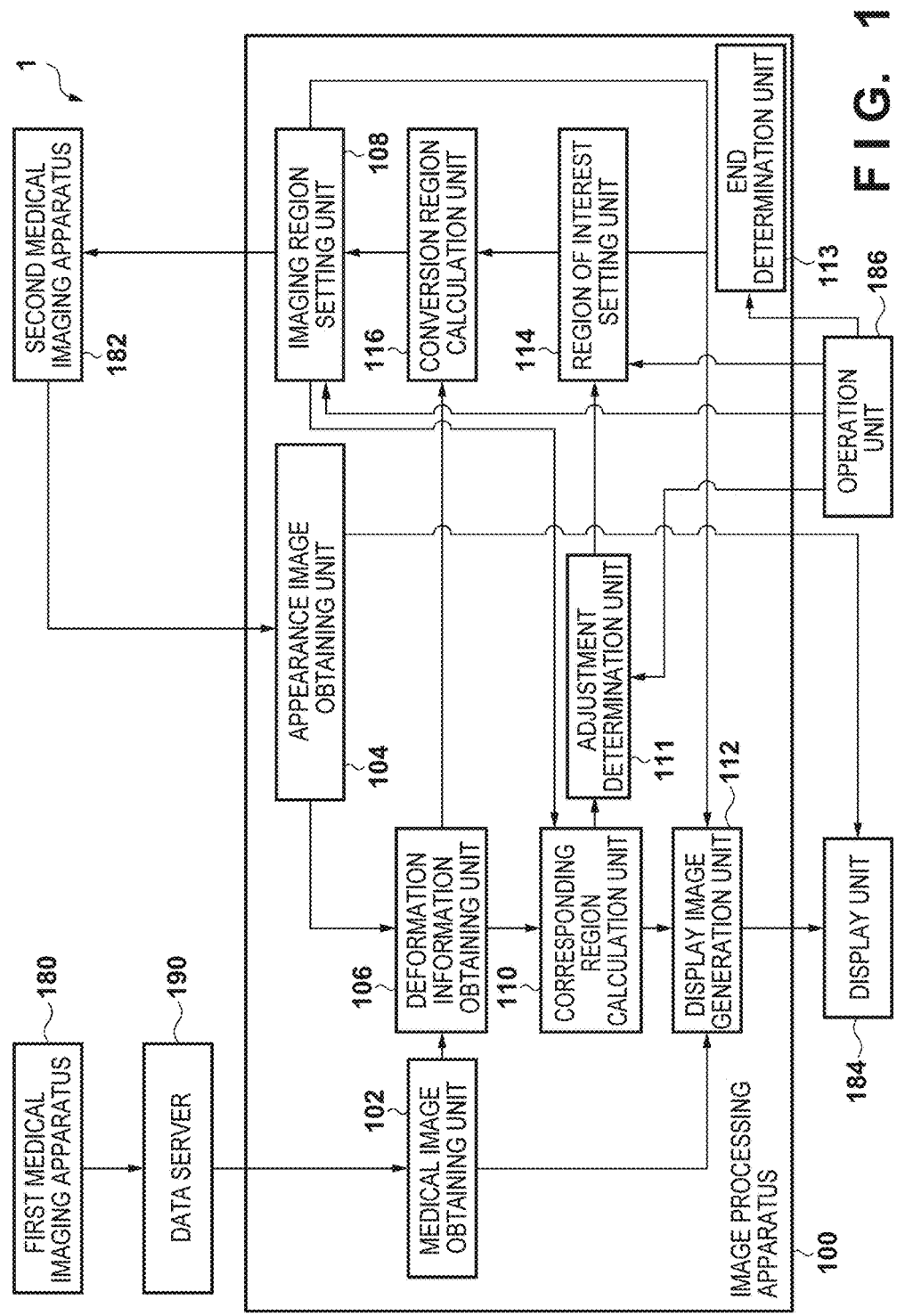
FIG. 1 shows functional configurations of an image diagnostic system and an image processing apparatus according to a first embodiment.

FIG. 1 shows a configuration of an image diagnostic system 1 according to the present embodiment. The image diagnostic system 1 includes an image processing apparatus 100, a first medical imaging apparatus 180, a second medical imaging apparatus 182, a display unit 184, an operation unit 186, and a data server 190.

Figure 2:
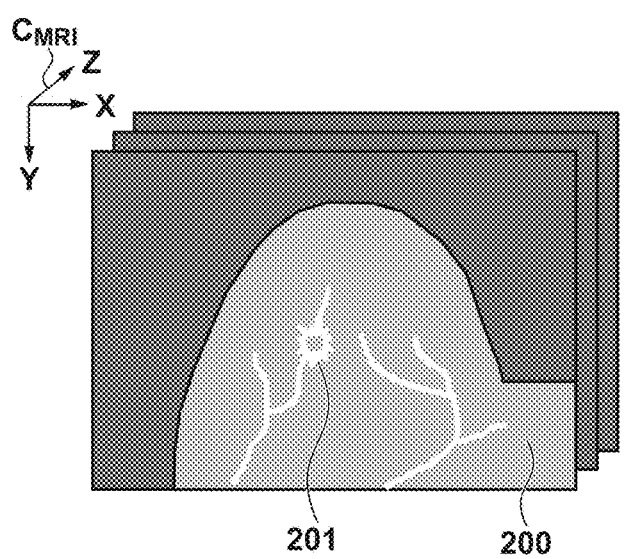
FIG. 2 is a schematic diagram showing an MRI image of an object.

The first medical imaging apparatus 180 is an MRI apparatus, and obtains an MRI image (first image) by imaging a breast of an examinee in a prone position, which is one example of a first shape state (an upheld state in which the breast is not held by flat plates). FIG. 2 is a schematic diagram showing a two-dimensional image obtained by slicing a three-dimensional MRI image of the breast captured by the first medical imaging apparatus 180 along a cross-section perpendicular to a craniocaudal direction (a direction from the head side to the feet side) of the examinee (axial cross-section). It is assumed that, in the present embodiment, an MRI image coordinate system C_MRI is defined as follows: one point in an MRI image 200 is the origin, an axis representing a direction from the right hand to the left hand of the examinee is an X-axis, an axis representing a direction from the anterior side to the posterior side of the examinee is a Y-axis, and an axis representing a direction from the feet to the head of the examinee is a Z-axis.

Figure 3:
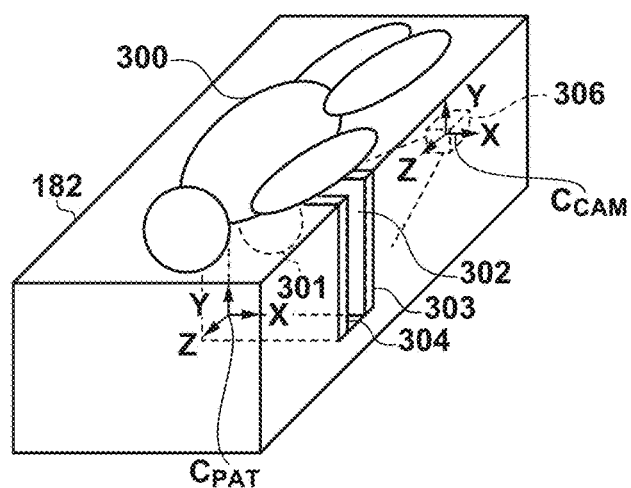
FIG. 3 is a schematic diagram showing a situation in which imaging is performed by a PAT apparatus according to the first embodiment.

The second medical imaging apparatus 182 is a photoacoustic tomography imaging apparatus (PAT apparatus), and obtains a PAT image (second image) by imaging the breast of the examinee in a second shape state (a held state in which the breast is held by the flat plates) through irradiation with near infrared ray pulses within a range of an imaging region set by a later-described imaging region setting unit 108 of the image processing apparatus 100. FIG. 3 is a schematic diagram showing a situation in which imaging is performed by the second medical imaging apparatus 182. As shown in FIG. 3, an examinee 300 takes a prone position on a bed on an upper surface of the second medical imaging apparatus 182. An object, that is to say, a breast 301 on one side is inserted into an opening 302 of the upper surface of the second medical imaging apparatus 182. At this time, in order for irradiation light to reach the internal parts of the breast, the breast is held in a state where it is pressurized by two transparent holding plates (a holding plate 303 on the feet side and a holding plate 304 on the head side), and imaged in a state where the thickness thereof is reduced. It is assumed that, in the present embodiment, the holding plate 303 and the holding plate 304 are both flat plates, and surfaces thereof that come into contact with the breast (hereinafter referred to as holding surfaces) are planar surfaces. The near infrared ray pulses, which represent irradiation light, are emitted by a non-illustrated light source in a direction orthogonal to the planar surfaces of the holding plates 303, 304. Photoacoustic signals generated inside the body in response to irradiation with the near infrared ray pulses are received by a non-illustrated ultrasound probe that is arranged to be orthogonal to the planar surfaces of the holding plates 303, 304. In the present embodiment, a PAT apparatus coordinate system C_PAT is defined as follows. A plane parallel to the holding plates 303, 304 is an XY-plane, an axis representing a direction from the right hand to the left hand of the examinee is an X-axis, and an axis representing a direction from the anterior side to the posterior side of the examinee is a Y-axis. Also, a normal direction of the holding plates 303, 304 is a Z-axis, and a direction from the feet to the head of the examinee is a positive direction along the Z-axis. In addition, a lower end position on the right-hand side of the inner planar surface of the holding plate 303 is the origin.

Furthermore, a camera 306 for capturing an appearance image of the breast (third image) is mounted on the second medical imaging apparatus 182. The camera 306 is placed in a position in which the appearance of the breast can be imaged through the holding plate 303 from the feet side. C_CAM denotes a camera coordinate system in which a position of a focal point of the camera 306 is the origin. It is assumed here that the camera 306 has already been calibrated in the PAT apparatus coordinate system C_PAT. It is also assumed that a coordinate conversion matrix T_CtoP from the camera coordinate system C_CAM to the PAT apparatus coordinate system C_PAT and internal parameters of the camera, which have been obtained through the camera calibration, are held by the image processing apparatus 100 as known information.

Figure 4:
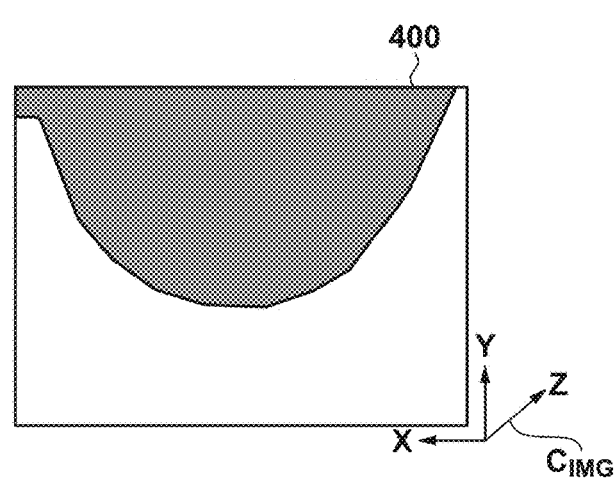
FIG. 4 is a schematic diagram showing an appearance image captured by a camera mounted on the PAT apparatus.

FIG. 4 is a schematic diagram showing an appearance image 400 of the breast captured by the camera 306. It is assumed that, in the present embodiment, a lower right end of the appearance image 400 is the origin of an appearance image coordinate system C_IMG, and the appearance image 400 lies on a plane at Z=0. It should be noted that conversion from the camera coordinate system C_CAM into the appearance image coordinate system C_IMG can be carried out using general methods, and therefore a description thereof is omitted.

The display unit 184 displays an imaging region setting screen for setting an imaging region, a region of interest setting screen for setting a region of interest, and a display image generated by the image processing apparatus 100. The operation unit 186 is a mouse, a keyboard, a physical switch, and the like, and accepts operational input from an operator.

The data server 190 holds MRI images 200 obtained by the first medical imaging apparatus 180, and these MRI images 200 are input to the image processing apparatus 100 via a later-described medical image obtaining unit 102 of the image processing apparatus 100.

<Configurations of Functional Blocks of Image Processing Apparatus 100>

The image processing apparatus 100 is connected to the data server 190, the second medical imaging apparatus 182, the display unit 184, and the operation unit 186. The image processing apparatus 100 includes the medical image obtaining unit 102, an appearance image obtaining unit 104, a deformation information obtaining unit 106, the imaging region setting unit 108, a corresponding region calculation unit 110, an adjustment determination unit 111, a display image generation unit 112, an end determination unit 113, a region of interest setting unit 114, and a conversion region calculation unit 116, and the operations of the functional blocks are controlled by a non-illustrated CPU reading and executing a program.

The medical image obtaining unit 102 obtains an MRI image 200 input to the image processing apparatus 100, and outputs this MRI image 200 to the deformation information obtaining unit 106 and the display image generation unit 112.

The appearance image obtaining unit 104 obtains an appearance image 400 input to the image processing apparatus 100, and outputs this appearance image 400 to the deformation information obtaining unit 106, the imaging region setting unit 108, and the display unit 184.

The deformation information obtaining unit 106 calculates and obtains deformation information by deforming and positioning the MRI image 200 with respect to the appearance image 400, and outputs this deformation information to the corresponding region calculation unit 110.

The imaging region setting unit 108 sets an imaging region for capturing a PAT image on the imaging region setting screen displayed on the display unit 184, and outputs information of this imaging region to the corresponding region calculation unit 110, the display image generation unit 112, and the second medical imaging apparatus 182.

The corresponding region calculation unit 110 calculates, based on the deformation information obtained by the deformation information obtaining unit 106, a corresponding region in the MRI image 200 corresponding to the imaging region set by the imaging region setting unit 108, and outputs information of this corresponding region to the display image generation unit 112 and the region of interest setting unit 114.

Based on an operation of the operator on the operation unit 186, the adjustment determination unit 111 determines whether or not to set a region of interest by adjusting the corresponding region obtained by the corresponding region calculation unit 110. The necessity of such setting is determined by, for example, the operator clicking a setting button arranged on a non-illustrated monitor using a non-illustrated mouse and the like so as to perform input indicating whether or not to set the region of interest by adjusting the corresponding region.

The display image generation unit 112 generates an image to be displayed on the imaging region setting screen by overlapping the imaging region over the appearance image 400. It also generates an image to be displayed on the region of interest setting screen based on the MRI image 200 and one of the corresponding region and the region of interest. These images are output to the display unit 184.

The end determination unit 113 determines whether or not to end a process for setting the imaging region based on an operation on the operation unit 186.

The region of interest setting unit 114 sets the region of interest by adjusting the corresponding region on the region of interest setting screen of the display unit 184, and outputs this region of interest to the display image generation unit 112 and the conversion region calculation unit 116.

The conversion region calculation unit 116 calculates a corresponding region (hereinafter referred to as a conversion region) in the object in an imaging state corresponding to the region of interest, and outputs information of this conversion region to the imaging region setting unit 108.

It should be noted that the configurations of the above-described functional blocks are merely illustrative; a plurality of functional blocks may compose one functional block, and any of the functional blocks may be further divided into a plurality of functional blocks.

<Processing Executed by Image Processing Apparatus 100>

Figure 5:
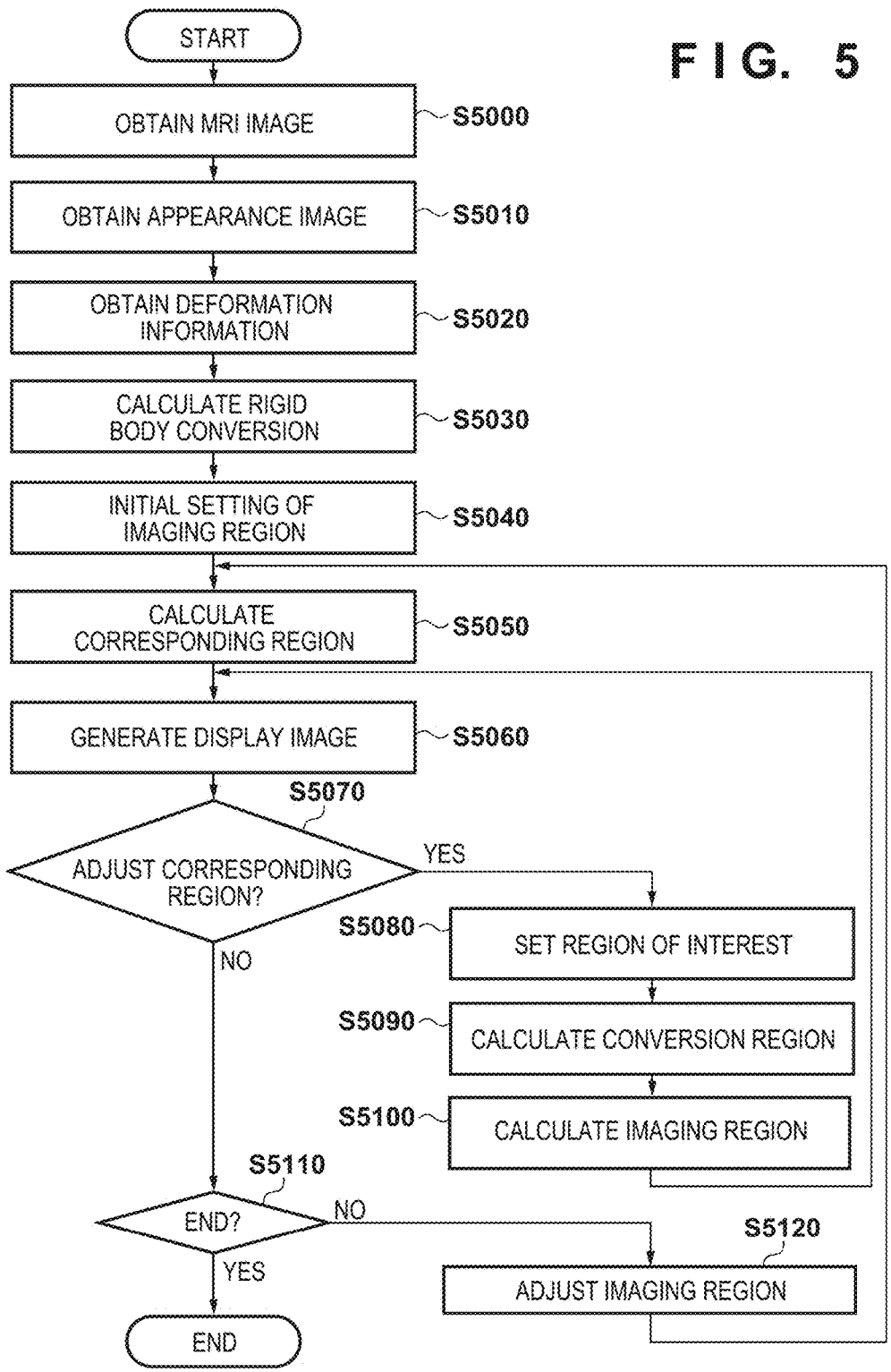
FIG. 5 is a flowchart showing a procedure of processing of the image processing apparatus according to the first embodiment.

Next, a description is given of a procedure of processing executed by the image processing apparatus 100 according to the present embodiment with reference to a flowchart of FIG. 5.

In step S5000, the medical image obtaining unit 102 obtains an MRI image 200 of a breast in a prone position input from the data server 190 to the image processing apparatus 100. It is assumed that, in the present embodiment, a nipple position in the MRI image 200 has been designated in advance.

In step S5010, the appearance image obtaining unit 104 obtains an appearance image 400 of the breast of the examinee input from the second medical imaging apparatus 182 to the image processing apparatus 100.

In step S5020, the deformation information obtaining unit 106 obtains deformation information for deforming the MRI image into the shape of the breast in the imaging state. In the present embodiment, a deformation function F $(x, y, z)$ representing deformation from a pre-hold state to a post-hold state, as well as a deformation function $F^{-1}$ $(x, y, z)$ representing inverse deformation from the post-hold state to the pre-hold state, is obtained by deforming and positioning the MRI image 200 with respect to the appearance image 400. It is assumed that these deformation functions are used as the deformation information. This positioning can be performed using, for example, a technique in which a post-deformation breast shape, which is obtained by applying to an MRI image a simulation of physical deformation caused by pressurization with flat plates, is evaluated based on a two-dimensional breast shape extracted from an X-ray mammography image, as disclosed in C. Tanner, et al., "Breast Shapes on Real and Simulated Mammograms", Proc. Int. Workshop on Digital Mammography 2010 (IWDM 2010), LNCS 6136, pp. 540-547, 2010.

It should be noted that the present embodiment is based on the premise that the posture of the examinee in the PAT image coordinate system C_PAT substantially matches the posture of the examinee in the MRI image coordinate system C_MRI. That is to say, it is assumed that the breast is compressed by the two holding plates 303, 304 along a Z-axis direction of the MRI image coordinate system C_MRI. It is also assumed that a measured value of the distance between the two holding plates (the thickness of the post-hold breast), d, is input from the second medical imaging apparatus 182 to the image processing apparatus 100, and information thereof is used at the time of the physical deformation simulation. It is further assumed that the deformation functions F $(x, y, z)$ and $F^{-1}$ $(x, y, z)$ are calculated such that the nipple position is the same in the pre-hold state and in the post-hold state.

It should be noted that the deformation functions are not limited to being calculated by deforming and positioning the MRI image 200 with respect to the appearance image 400, and may be calculated using any other method. For example, instead of capturing the appearance image 400 with the camera 306, an external shape of the breast may be obtained using a non-illustrated ranging sensor, and the MRI image 200 may be deformed and positioned with respect to the external shape of the breast. Alternatively, an ultrasound image of the internal parts of the breast may be captured with a non-illustrated ultrasound image obtaining unit provided in the second medical imaging apparatus 182, and the MRI image 200 may be deformed and positioned with respect to the ultrasound image.

In step S5030, the deformation information obtaining unit 106 obtains rigid body conversion between the MRI image coordinate system C_MRI and the PAT apparatus coordinate system C_PAT. That is to say, a coordinate conversion matrix T_MtoP from the MRI image coordinate system C_MRI to the PAT apparatus coordinate system C_PAT is derived. It is assumed that all of the coordinate conversion matrices described below, including T_MtoP, are 4×4 matrices representing translation and rotation of a coordinate system. The present embodiment is based on the premise that the posture of the examinee in the PAT apparatus coordinate system C_PAT substantially matches the posture of the examinee in the MRI image coordinate system C_MRI, and it is assumed that coordinate conversion from the MRI image coordinate system C_MRI into the PAT apparatus coordinate system C_PAT can be expressed only by way of translation. Under this premise, translational components of T_MtoP are calculated such that the nipple position in the MRI image 200 obtained in step S5000 matches the nipple position of the examinee in the PAT apparatus coordinate system C_PAT.

Here, the nipple position in the PAT apparatus coordinate system C_PAT can be obtained using, for example, a non-illustrated ranging apparatus placed in a position in which the breast can be measured from a lower side of the opening 302 of the second medical imaging apparatus 182. That is to say, the nipple position in the PAT apparatus coordinate system C_PAT can be obtained by a user manually designating the nipple position in a range image of the breast captured by the ranging apparatus using a non-illustrated mouse, keyboard, and the like. It is assumed that, at this time, the ranging apparatus has already been calibrated in the PAT apparatus coordinate system C_PAT. It should be noted that the nipple position in the PAT apparatus coordinate system C_PAT is not limited to being obtained using the ranging apparatus, and may be obtained using other apparatuses and means capable of measuring three-dimensional positions, such as a digitizer and a stereo camera.

Figure 6:
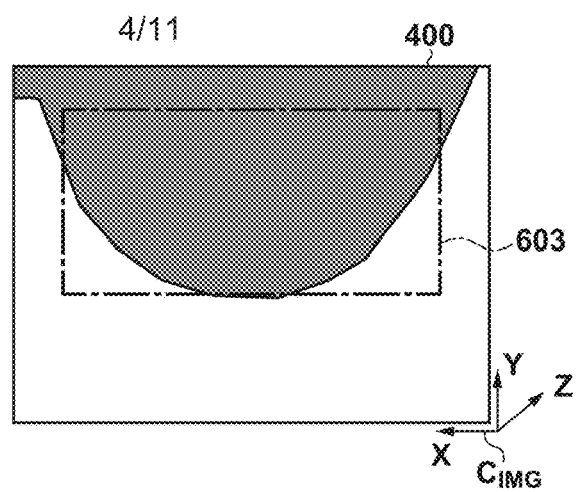
FIG. 6 is a schematic diagram showing an imaging region according to the first embodiment.

In step S5040, the imaging region setting unit 108 configures initial setting of an imaging region of the second medical imaging apparatus 182. For example, an oblong including the entirety of a range in which a PAT image can be captured by the second medical imaging apparatus 182 is set on the appearance image 400 as an initial value of the imaging region. It is assumed that, in the present embodiment, an imaging region 603 is set in the appearance image coordinate system C_IMG as shown in FIG. 6. Then, based on the initial value of the imaging region in the appearance image coordinate system C_IMG, an imaging region in the PAT apparatus coordinate system C_PAT is obtained. For example, four vertices of the set imaging region are first converted into four points in the camera coordinate system C_CAM, four intersections between the holding plate 303 and four straight lines connecting these four points and the origin of the camera coordinate system are obtained, and the four intersections are converted into four points in the PAT apparatus coordinate system C_PAT. Then, a rectangle circumscribing these four points is regarded as an imaging region in the PAT apparatus coordinate system C_PAT.

In step S5050, the corresponding region calculation unit 110 calculates a corresponding region in the MRI image 200 corresponding to the imaging region in the PAT apparatus coordinate system C_PAT. Specifically, first, rigid body conversion from the imaging region in the PAT apparatus coordinate system C_PAT into a region in the MRI image coordinate system C_MRI is carried out using an inverse conversion of the rigid body conversion (the coordinate conversion matrix T_MtoP) calculated in step S5030 (an inverse matrix of T_MtoP). Next, by applying deformation processing to this region using the deformation function $F^{-1}$ (x, y, z) obtained in step S5020, a corresponding region in the MRI image coordinate system C_MRI is calculated.

It should be noted that, in consideration of error in the deformation information calculated in step S5020, the calculated corresponding region may be adjusted to be small. For example, a predetermined value may be subtracted as a margin. Also, the deformation information calculated in step S5020 may include information related to error in calculation of the deformation information (e.g., a positioning residual), and the subtracted margin may be decided on based on this information related to error. For example, the corresponding region in the MRI image coordinate system C_MRI can be calculated by re-setting each face of a three-dimensional imaging region to be smaller by the margin. This makes it possible to determine whether or not a region of attention, such as a tumor, is included in the corresponding region more rigorously, and hence to prevent a part of a region of attention, such as the tumor, from deviating from the imaging region.

In step S5060, the display image generation unit 112 generates a display image by overlapping the imaging region (the imaging region 603 in FIG. 6) over the appearance image 400, and outputs this display image to the display unit 184. Here, the imaging region 603 may be displayed in a frame line as shown in FIG. 6, and the inside of the region may be filled with a predetermined color and texture of predetermined transparency. Furthermore, the user may be enabled to adjust the type of the frame line, the filling color and texture, the transparency, and the like using the non-illustrated mouse, keyboard, and the like.

Figure 7A:
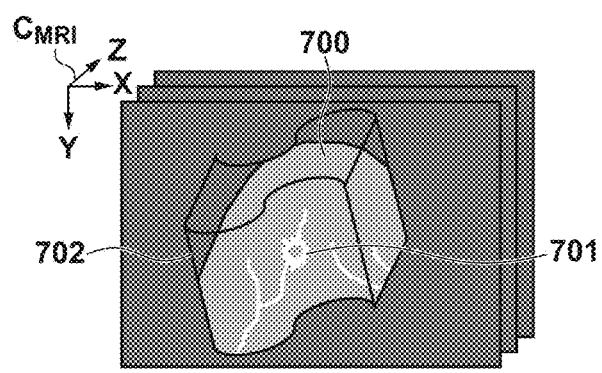
FIGS. 7A to 7C are schematic diagrams showing examples of a display image according to the first embodiment.
Figure 7B:
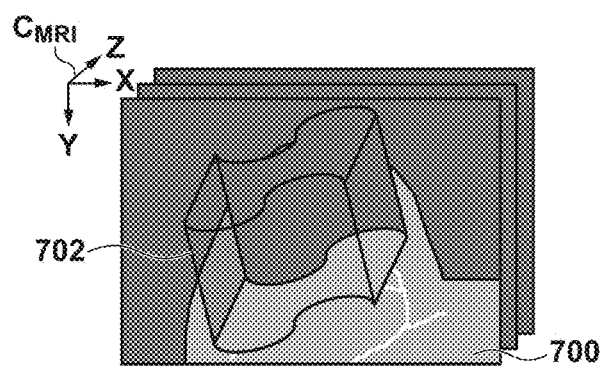
Figure 7C:
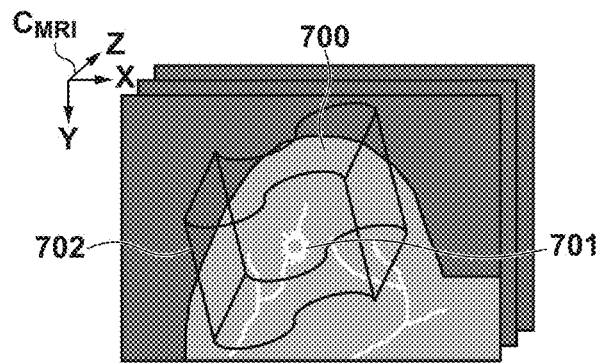

Furthermore, based on the MRI image 200 and the corresponding region (or a region of interest set in the later-described step S5080), the display image generation unit 112 generates an image to be displayed on the imaging region setting screen of the display unit 184. For example, as shown in FIG. 7A, a volume rendering image (MRI_VR image) 700 of the MRI image inside a corresponding region 702 (or a region of interest) is generated. That is to say, the display image generation unit 112 generates a volume rendering image of the first image (MRI image 200) inside the corresponding region. In this case, whether or not a region of attention, such as a tumor 701, is included inside the corresponding region 702 (or the region of interest) can be confirmed. Conversely, as shown in FIG. 7B, an MRI_VR image 700 outside the corresponding region 702 (or the region of interest) may be generated. That is to say, the display image generation unit 112 may generate a volume rendering image of the first image (MRI image 200) outside the corresponding region. In this case, whether or not a part of a region of attention, such as the tumor 701, is deviating from the corresponding region 702 (or the region of interest) can be confirmed. Alternatively, as shown in FIG. 7C, an image may be generated by overlapping an MRI_VR image 700 of the entire MRI image and a graphic showing the corresponding region 702 (or the region of interest).

In step S5070, based on a user operation via the operation unit 186, the adjustment determination unit 111 determines whether or not to set a region of interest by adjusting the corresponding region in the MRI image coordinate system C_MRI. For example, determination information indicating whether or not to set the region of interest by adjusting the corresponding region is input by, for example, the operator clicking a setting button arranged on the non-illustrated monitor using the non-illustrated mouse and the like. Alternatively, it may be determined that the region of interest is to be set by adjusting the corresponding region when a non-illustrated mouse cursor has moved onto the display image generated in step S5060. If it is determined that the region of interest is to be set by adjusting the corresponding region, processing proceeds to step S5080. On the other hand, if it is determined that the region of interest is not to be set by adjusting the corresponding region, processing proceeds to step S5100.

In step S5080, the region of interest setting unit 114 adjusts the corresponding region in the MRI image coordinate system C_MRI based on a user operation via the operation unit 186. Then, it newly sets the adjusted region as a region of interest. For example, the corresponding region can be adjusted (enlarged and reduced) by displaying the display image generated in step S5060 on the display unit 184 and moving vertices, lines, and faces of a graphic showing the corresponding region on the displayed image using the non-illustrated mouse. Alternatively, the adjustment may be made by moving the entirety of the corresponding region using the non-illustrated mouse. Furthermore, the adjustment may be made by inputting a movement amount, an enlargement ratio, and the like of the entire corresponding region using the non-illustrated keyboard.

In step S5090, the conversion region calculation unit 116 calculates a region (conversion region) on the object in the imaging state corresponding to the region of interest set in step S5080. Specifically, first, by applying deformation processing to the region of interest in the MRI image coordinate system C_MRI using the deformation function F (x, y, z) obtained in step S5020, the region of interest is converted into a region of a post-hold shape state in the MRI image coordinate system C_MRI. Then, rigid body conversion into a region in the PAT apparatus coordinate system C_PAT (conversion region) is carried out using the coordinate conversion matrix T_MtoP calculated in step S5030.

It should be noted that the conversion region may be calculated after the setting of the region of interest is completed, instead of calculating the conversion region each time the setting of the region of interest is changed. It is sufficient to input the determination to complete the setting by, for example, the operator clicking a completion button arranged on the non-illustrated monitor using the non-illustrated mouse.

In step S5100, based on the conversion region calculated in step S5090, the imaging region setting unit 108 calculates an imaging region of a PAT image captured by the second medical imaging apparatus 182. Specifically, a cuboid circumscribing the conversion region calculated in step S5090 is calculated, and this cuboid is newly regarded as a three-dimensional imaging region. It is assumed that line segments of the cuboid are parallel to corresponding axes of the PAT apparatus coordinate system C_PAT, and two faces parallel to the XY-plane lie on Z=0 and Z=d.

Here, in consideration of error in the deformation information calculated in step S5020, the imaging region may be adjusted to be large. For example, a predetermined value may be added as a margin. Also, the deformation information calculated in step S5010 may include information related to error in calculation of the deformation information (e.g., a positioning residual), and the added margin may be decided on based on this information related to error. For example, among the faces of the three-dimensional imaging region, four faces other than the two faces parallel to the XY-plane are re-set to be larger by the margin. This makes it possible to prevent a part of a region of attention, such as a tumor 701, from deviating from the imaging region.

It should be noted that the imaging region in the PAT apparatus coordinate system C_PAT may further be converted into an imaging region in the appearance image coordinate system C_IMG and displayed on the imaging region setting screen of the display unit 184 together with the appearance image 400. In this case, the imaging region in the PAT apparatus coordinate system C_PAT is first converted into an imaging region in the camera coordinate system C_CAM using the inverse matrix of the coordinate conversion matrix T_CtoP from the camera coordinate system C_CAM to the PAT apparatus coordinate system C_PAT. Then, it is sufficient to calculate the imaging region in the appearance image coordinate system C_IMG through conversion from the camera coordinate system C_CAM into the appearance image coordinate system C_IMG.

In step S5110, the end determination unit 113 determines whether or not to end a process for setting the imaging region based on an operation on the operation unit 186. For example, it determines to end the process when the operator clicks an end button arranged on the non-illustrated monitor using the non-illustrated mouse. If it determines to end the process, it causes processing of the image processing apparatus 100 to end. On the other hand, if it does not determine to end the process, processing proceeds to step S5120 and the setting of the imaging region is executed.

In step S5120, based on an operation on the operation unit 186, the imaging region setting unit 108 adjusts the imaging region of the PAT image captured by the second medical imaging apparatus 182. Specifically, the appearance image 400 is displayed on the display unit 184, and the user manually adjusts a range of the set imaging region 603 (two-dimensional rectangular region) on the displayed image using the non-illustrated mouse, keyboard, and the like. It is assumed that, in the present embodiment, a mark indicating a region of attention, such as a tumor, is drawn on a body surface of an object (e.g., a breast) with a pen and the like, and the user adjusts the range of the imaging region 603 such that it includes, for example, the entirety of this mark based on information that the user has visually confirmed on the displayed image. That is to say, the imaging region setting unit 108 re-sets the imaging region by accepting input of the imaging region 603 on the third image (the appearance image 400) based on a user operation via the operation unit 186.

Furthermore, based on the imaging region 603 in the appearance image coordinate system C_IMG, the imaging region in the PAT apparatus coordinate system C_PAT is obtained through a process similar to step S5040. For example, four vertices of the imaging region 603 are converted into four points in the camera coordinate system C_CAM, four intersections between the holding plate 303 and four straight lines connecting these four points and the origin of the camera coordinate system are obtained, and the four intersections are converted into four points in the PAT apparatus coordinate system C_PAT. Then, a rectangle circumscribing these four points is set as the imaging region in the PAT apparatus coordinate system C_PAT. Here, a cuboid region formed by pushing an imaging region (a rectangular region) on a two-dimensional plane at Z=0 in the PAT apparatus coordinate system C_PAT from Z=0 to Z=d (the distance between the post-hold flat plates) is set as the three-dimensional imaging region. Thereafter, processing returns to step S5050, and subsequent processes are repeated. That is to say, the corresponding region calculation unit 110 re-calculates the corresponding region in accordance with the re-setting of the imaging region in step S5050, and the display image generation unit 112 re-generates the display image in accordance with the re-calculation of the corresponding region in step S5060.

The processing sequence of the image processing apparatus 100 is executed in the above-described manner. Thereafter, the second medical imaging apparatus 182 captures a PAT image based on the set imaging region.

As described above, the image processing apparatus 100 according to the present embodiment includes a first image obtaining unit (the medical image obtaining unit 102) that obtains a first image (the MRI image 200) of an object (e.g., a breast) in the first shape state (an upheld state), the imaging region setting unit 108 that sets an imaging region (the imaging region 603) of the object in the second shape state (a held state in which the object is held by the holding plates 303, 304), the deformation information obtaining unit 106 that obtains deformation information (a deformation function) indicating deformation of the object from the second shape state (the held state) to the first shape state (the unheld state), the corresponding region calculation unit 110 that calculates a corresponding region (the corresponding region 702) in the first shape state (the unheld state) corresponding to the imaging region (the imaging region 603) based on the deformation information (the deformation function), and the display image generation unit 112 that generates a display image (an MRI_VR image, an MIP image) based on the first image (the MRI image 200) and the corresponding region (the corresponding region 702).

In this way, when setting an imaging region of a PAT image, a corresponding region that corresponds to this imaging region can be displayed on an MRI image of the object, thereby allowing for visualization of a range to be imaged out of a reference image, such as an MRI image. Therefore, the user can adjust the imaging region while confirming the display.

In this way, in the present embodiment, an imaging region of a PAT image can be set such that a region of attention, such as a tumor, inside the object is imaged appropriately.

The image processing apparatus 100 according to the present embodiment also includes the region of interest setting unit 114 that sets a region of interest by adjusting a corresponding region (the corresponding region 702) (by, for example, enlarging and reducing the corresponding region), and the conversion region calculation unit 116 that calculates a conversion region in the second shape state (held state) corresponding to the region of interest by deforming the set region of interest based on the deformation information, and the imaging region setting unit 108 sets an imaging region of the object based on the calculated conversion region.

In this way, after the region of interest in which the user is more interested is set by adjusting the range of the corresponding region in a reference image, such as an MRI image, an imaging region can be set such that it includes this region of interest (such that a region of attention, such as a tumor, inside the object is imaged appropriately).

While the present embodiment has described an exemplary case in which a breast of a human body is regarded as an object, embodiments of the present invention are not limited in this way, and any object may be used.

Modification Example 1

While the present embodiment has described an exemplary case in which a corresponding region or an imaging region is re-set based on information related to error in calculation of deformation information, embodiments of the present invention are not limited in this way. For example, the image processing apparatus 100 may hold a predetermined margin as known information in advance, and a calculated region may be re-set based on this predetermined margin. At this time, a value of a predetermined margin used to re-set a corresponding region to be small may be different from a value of a predetermined margin used to re-set an imaging region to be large.

Furthermore, a predetermined value may be set also in consideration of a PAT image reconstruction method. For example, when a reconstruction method is used that allows for reconstruction over a range larger than an imaging region, the predetermined value may be set to a small value.

Modification Example 2

While the present embodiment has described an exemplary case in which a corresponding region and an imaging region are re-set based on information related to error in calculation of deformation information, embodiments of the present invention are not limited in this way. For example, another region that is different from the corresponding region and the imaging region may be newly set and displayed in a mode different from the corresponding region and the imaging region. In this case, a three-dimensional volume rendering image of an MRI image may be displayed based on the newly set region. Alternatively, it may be displayed based on both of the newly set region and a three-dimensional imaging region; at this time, a region between the newly set region and the three-dimensional imaging region may be displayed as a volume rendering image in a different mode.

Modification Example 3

While the present embodiment has described an exemplary case in which a three-dimensional volume rendering image of an MRI image is displayed based on a three-dimensional corresponding region, embodiments of the present invention are not limited in this way. For example, an axial cross-section (XY-plane) of an MRI image and a graphic obtained by cutting out a three-dimensional corresponding region along the axial cross-section may be displayed. Also, only the inside or outside of the corresponding region along the axial cross-section may be displayed. At this time, an axial cross-section including the tumor 701 may be selected and displayed, or axial cross-sections between Z=0 and Z=d (the distance between the post-hold flat plates) may be displayed in sequence so as to enable confirmation of whether or not the entirety of the tumor 701 is included. Also, confirmation of a corresponding region is not limited to being enabled on an axial cross-section of an MRI image, and may be enabled on a sagittal cross-section (YZ-plane) and a coronal cross-section (XZ-plane). Furthermore, confirmation of a corresponding region is not limited to being enabled on an axial cross-section, a sagittal cross-section, and a coronal cross-section of a deformation MRI image, and may be enabled on any cross-section including a curved cross-section. Moreover, a cross-sectional image according to the present modification example may be a maximum value projection image (an MIP (maximum intensity projection) image) obtained by projecting a maximum pixel value within a predetermined range from a cross-section onto the cross-section. That is to say, the display image generation unit 112 may generate a volume rendering image or a maximum value projection image of a first image (an MRI image) outside or inside a corresponding region.

Modification Example 4

While the present embodiment has described an exemplary case in which an MRI apparatus is used as the first medical imaging apparatus 180, embodiments of the present invention are not limited in this way. For example, an X-ray CT (computed tomography) apparatus, a PET (positron emission tomography)/SPECT (single photon emission CT) apparatus, a three-dimensional ultrasound apparatus, and the like can be used thereas. Also, any other modality may be used thereas. In this case, a first image includes various images, such as an X-ray CT image, a tomography image, and an ultrasound image. When these modalities are used, it is sufficient to obtain the deformation function F (x, y, z) by not only estimating deformation by pressurization with flat plates, but also estimating deformation caused by differences in a body position for imaging (e.g., gravitational deformation from a supine position to a prone position). It should be noted that gravitational deformation from a supine position to a prone position can be estimated using, for example, a method based on a gravitational deformation simulation disclosed in Y. Hu, et al., "A statistical motion model based on biomechanical simulations", Proc. MICCAI 2008, Part I, LNCS 5241, pp. 737-744, 2008.

Also, the first medical imaging apparatus 180 and the second medical imaging apparatus 182 may be the same imaging apparatus, and images obtained by a PAT apparatus imaging the same object in the past may be regarded as a first image. Furthermore, while the present embodiment has described an exemplary case in which a PAT apparatus is used as the second medical imaging apparatus 182, embodiments of the present invention are not limited in this way. For example, an X-ray mammography apparatus, an ultrasound diagnostic apparatus, and any other modality may be used thereas.

Modification Example 5

While the present embodiment has described an exemplary case in which the initial setting and adjustment of the imaging region 603 of a PAT image captured by the second medical imaging apparatus 182 are configured on the appearance image 400, embodiments of the present invention are not limited in this way. For example, coordinate values of four vertices indicating an imaging region in the PAT apparatus coordinate system C_PAT may be input directly using the non-illustrated keyboard and the like.

Second Embodiment

A second embodiment describes a case in which an imaging region of a PAT image is automatically set based on a region of interest set in an MRI image. The following describes an image processing apparatus according to the present embodiment, centering on differences from the first embodiment.

<Configuration of Image Diagnostic System 8>

Figure 8:
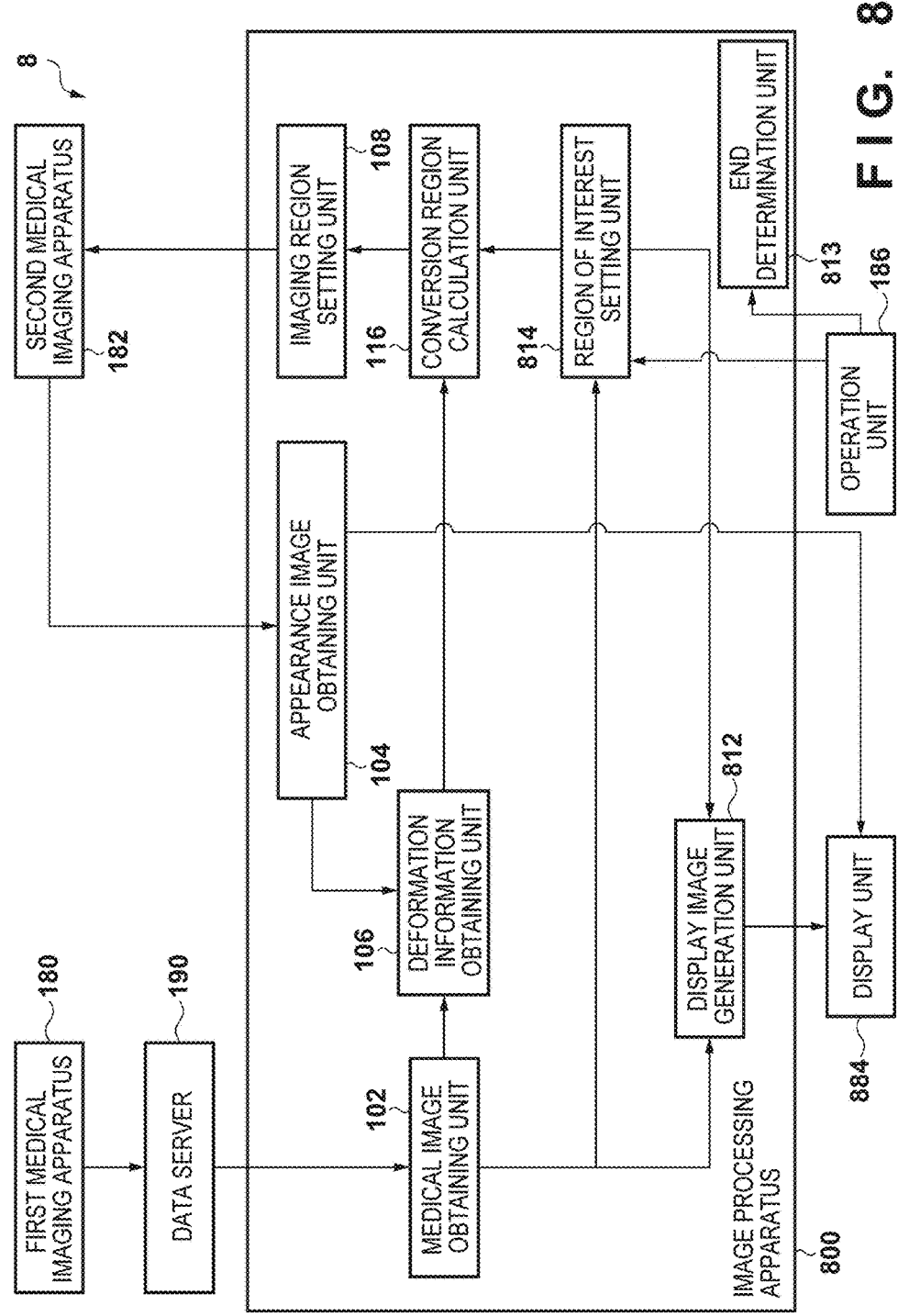
FIG. 8 shows functional configurations of an image diagnostic system and an image processing apparatus according to a second embodiment.

FIG. 8 shows a configuration of an image diagnostic system 8 according to the present embodiment. It should be noted that processing units that have the same functions as those in FIG. 1 are given the same numbers and signs thereas, and a description thereof is omitted.

The image diagnostic system 8 includes an image processing apparatus 800, a first medical imaging apparatus 180, a second medical imaging apparatus 182, a display unit 884, an operation unit 186, and a data server 190.

<Configurations of Functional Blocks of Image Processing Apparatus 800>

The image processing apparatus 800 is connected to the data server 190, the second medical imaging apparatus 182, the display unit 884, and the operation unit 186. The image processing apparatus 100 includes a medical image obtaining unit 102, an appearance image obtaining unit 104, a deformation information obtaining unit 106, an imaging region setting unit 108, a display image generation unit 812, an end determination unit 813, a region of interest setting unit 814, and a conversion region calculation unit 116. Here, the image processing apparatus 800 does not include the corresponding region calculation unit 110, which is included in the image processing apparatus 100 described in the first embodiment.

The display image generation unit 812 generates a display image based on an MRI image 200 that the medical image obtaining unit 102 has obtained from the data server 190 and on a region of interest set by the region of interest setting unit 814, and displays the display image on a region of interest setting screen of the display unit 884.

The end determination unit 813 determines whether or not to end a process of the region of interest setting unit 814 for setting a region of interest.

The region of interest setting unit 814 sets a region of interest on the region of interest setting screen of the display unit 884, and outputs information of this region of interest to the display image generation unit 812 and the conversion region calculation unit 116.

The display unit 884 displays the region of interest setting screen for setting a region of interest, and a display image generated by the image processing apparatus 800.

It should be noted that the configurations of the above-described functional blocks are merely illustrative; a plurality of functional blocks may compose one functional block, and any of the functional blocks may be further divided into a plurality of functional blocks.

<Processing Executed by Image Processing Apparatus 800>

Figure 9:
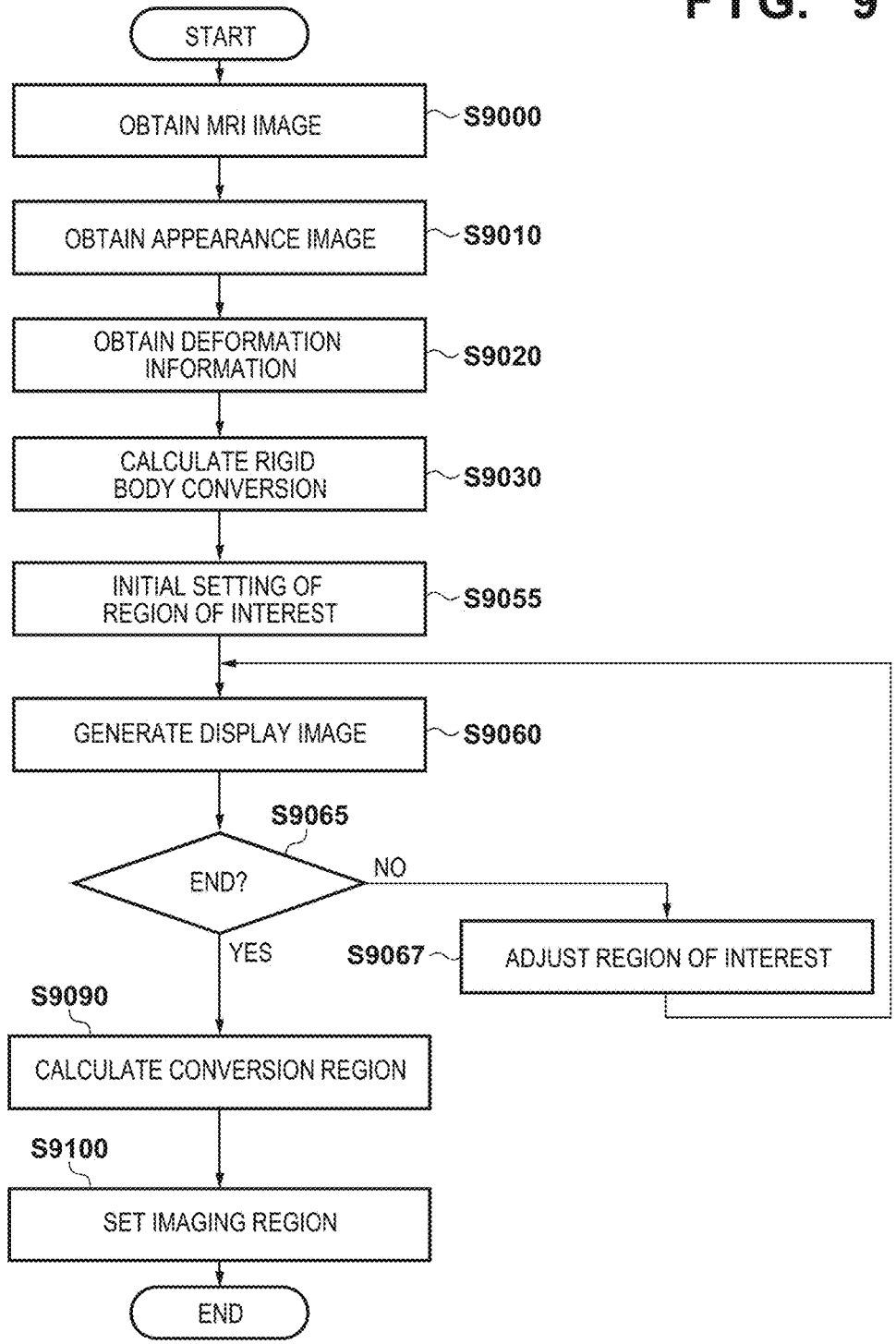
FIG. 9 is a flowchart showing a procedure of processing of the image processing apparatus according to the second embodiment.

Next, a description is given of a procedure of processing executed by the image processing apparatus 800 according to the present embodiment with reference to a flowchart of FIG. 9.

The processes of step S5040, step S5050, step S5070, step S5080, and step S5110, which are included in the processing executed by the image processing apparatus 100 according to the first embodiment described with reference to FIG. 5, are not executed in the present embodiment. The present embodiment differs in that processes of the later-described step S9060 and step S9100 are executed in place of the processes of step S5060 and step S5100. The present embodiment also differs in that step S9055 precedes the process of step S9060, and step S9065 and step S9067 follow the process of step S9060. Processes of step S9000 to step S9030 and step S9090 are similar to the processes of step S5000 to step S5030 and step S5090, respectively. The following description centers mainly on the differences.

First, in step S9055, the region of interest setting unit 814 configures initial setting of a region of interest in an MRI image coordinate system C_MRI. For example, a cuboid including the entirety of the MRI image 200 is set as an initial value of the region of interest.

Figure 10A:
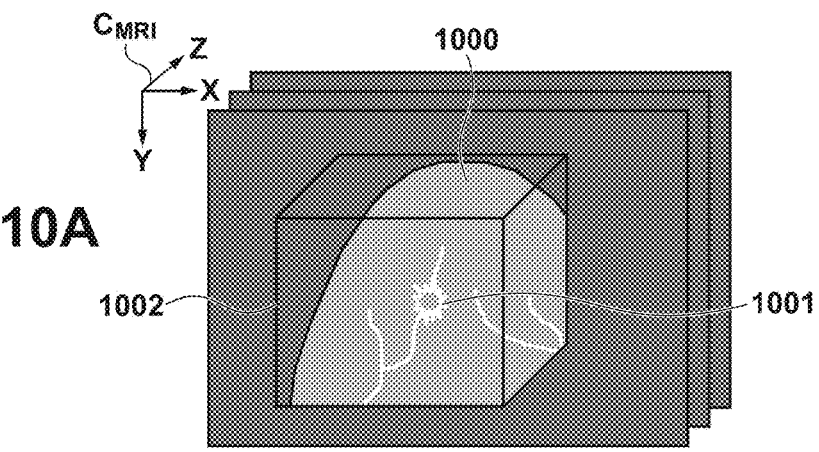
FIGS. 10A to 10C are schematic diagrams showing examples of a display image according to the second embodiment.
Figure 10B:
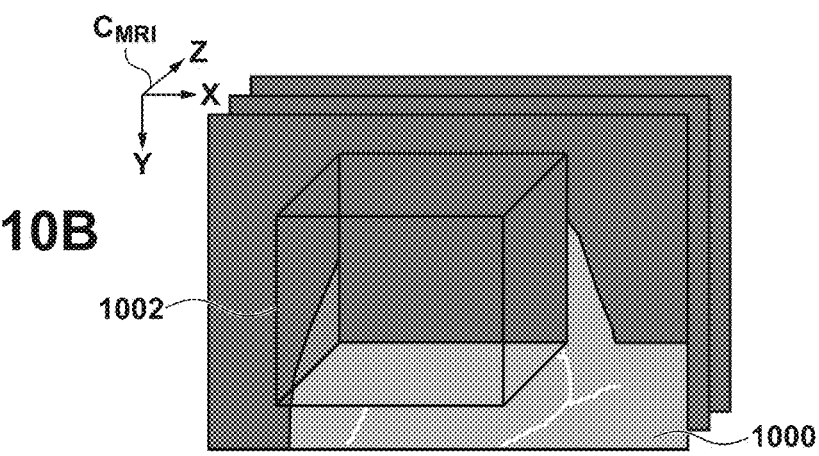
Figure 10C:
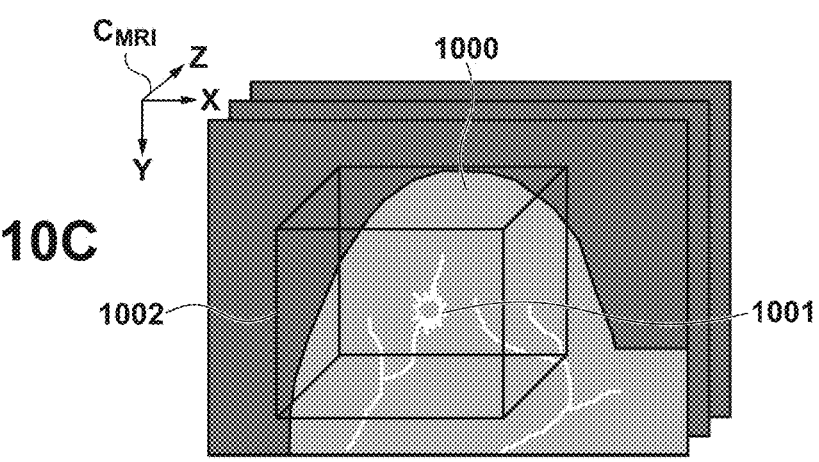

In step S9060, as shown in FIGS. 10A to 10C, the display image generation unit 812 generates a display image based on a volume rendering image (MRI_VR image) 1000 of the MRI image and a region of interest 1002, and displays the display image on the region of interest setting screen of the display unit 884. For example, it is sufficient to have the inside of the region of interest volume rendered and displayed as shown in FIG. 10A. In this case, whether or not a region of attention, such as a tumor 1001, is included inside the region of interest can be confirmed. Conversely, the outside of the region of interest may be volume rendered and displayed as shown in FIG. 10B. In this case, whether or not a part of the region of interest, such as the tumor 1001, is deviating from a corresponding region can be confirmed. Alternatively, as shown in FIG. 10C, a volume rendering image of the entire MRI image and a graphic showing the region of interest may be displayed in an overlapped manner.

In step S9065, the end determination unit 813 determines whether or not to end a process for setting the region of interest based on a user operation via the operation unit 186. For example, it determines to end the process when an operator clicks an end button arranged on a non-illustrated monitor using a non-illustrated mouse. If it determines to end the process, processing proceeds to step S9090. On the other hand, if it determines not to end the process, processing proceeds to step S9067.

In step S9067, the region of interest setting unit 814 adjusts a range of the region of interest in the MRI image coordinate system C_MRI based on a user operation via the operation unit 186. For example, the range of the region of interest is adjusted by displaying the display image generated in step S9060 on the region of interest setting screen of the display unit 884 and moving vertices, lines, and faces of a graphic showing the region of interest on the displayed image using the non-illustrated mouse. Alternatively, the adjustment may be made by moving the entirety of the region of interest using the non-illustrated mouse. Furthermore, the adjustment may be made by inputting a movement amount, an enlargement ratio, and the like of the entire region of interest using a non-illustrated keyboard. In this way, the region of interest setting unit 814 re-sets the region of interest 1002 by accepting input of the region of interest 1002 on a first image (the MRI image 200) based on a user operation. After the process of step S9067, processing returns to step S9060, and the display image generation unit 812 re-generates the display image.

In step S9100, based on a conversion region calculated in step S9090, which is a process similar to step S5090, the imaging region setting unit 108 sets an imaging region for a PAT image captured by the second medical imaging apparatus 182. Here, if the region of interest has been re-set in step S9067, the conversion region calculation unit 116 has re-calculated the conversion region in accordance with the re-setting of the region of interest 1002 in step S9090. In this case, in step S9100, the imaging region setting unit 108 re-sets the imaging region in accordance with the re-calculation of the conversion region. The specific substance of the process is similar to step S5100, and therefore a description thereof is omitted.

It should be noted that, in step S9020, the deformation information obtaining unit 106 may further obtain information related to error in estimation of deformation of an object from a first shape state to a second shape state, in addition to the deformation information. In this case, in step S9090, the conversion region calculation unit 116 may calculate the conversion region based on the deformation information and information related to the error.

The processing sequence of the image processing apparatus 800 is executed in the above-described manner. Thereafter, the second medical imaging apparatus 182 captures a PAT image based on the set imaging region.

As described above, the image processing apparatus 800 according to the present embodiment includes a first image obtaining unit (the medical image obtaining unit 102) that obtains a first image (the MRI image 200) of an object (e.g., a breast) in the first shape state (an unheld state), the region of interest setting unit 814 that sets a region of interest (the region of interest 1002) of the object on the first image (the MRI image 200), the deformation information obtaining unit 106 that obtains deformation information (a deformation function) indicating deformation of the object from the first shape state (the unheld state) to the second shape state (a held state in which the object is held by holding plates 303, 304), the conversion region calculation unit 116 that calculates a conversion region in the second shape state corresponding to the region of interest (the region of interest 1002) in the first shape state (the upheld state) based on the deformation information (the deformation function), and the imaging region setting unit 108 that sets an imaging region of the object in the second shape state (held state) based on the conversion region.

This makes it possible to set a region of interest in a reference image (an MRI image) obtained by imaging an object in a shape state that is different from a shape state at the time of capturing of a PAT image, and to automatically set an imaging region of the PAT image based on this region of interest. Also, as the user can adjust the region of interest while confirming the display, the imaging region can be set appropriately.

In this way, in the present embodiment, an imaging region of a PAT image and the like can be set such that a region of attention, such as a tumor, inside the object is imaged appropriately.

While the present embodiment has described an exemplary case in which a cuboid region of interest is set, embodiments of the present invention are not limited in this way, and a region of interest may have any shape, such as a cylindrical and an ellipsoidal shape. Also, a region of interest may be obtained by manually or automatically extracting an outline of a region of attention, such as a tumor. Furthermore, a region of a cuboid and the like enclosing the extracted region may be manually or automatically set, and this region may be regarded as a region of interest. It should be noted that modification examples similar to those of the first embodiment are applicable in the present embodiment.

Third Embodiment

While the first and second embodiments have described an exemplary case in which a PAT apparatus used as the second medical imaging apparatus 182 adopts a scheme whereby an object is held by two flat plates, embodiments of the present invention are not limited in this way, and any holding scheme may be used. The present embodiment describes a case in which a PAT apparatus is used that adopts a scheme whereby an object is held by pressing one holding member against a body in such a manner that the object is pressurized and thus thinned, instead of causing two holding members to hold the object therebetween. In particular, the present embodiment describes a case in which a stretchable holding film is used as a holding member. The following describes an image processing apparatus according to the present embodiment, centering on differences from the first embodiment.

<Configuration of Image Diagnostic System 11>

FIG. 11 shows a configuration of an image diagnostic system 11 according to the present embodiment. It should be noted that processing units that have the same functions as those in FIG. 1 are given the same numbers and signs thereas, and a description thereof is omitted.

The image diagnostic system 11 includes an image processing apparatus 1100, a first medical imaging apparatus 180, a second medical imaging apparatus 1182, a display unit 184, an operation unit 186, and a data server 190.

Figure 12:
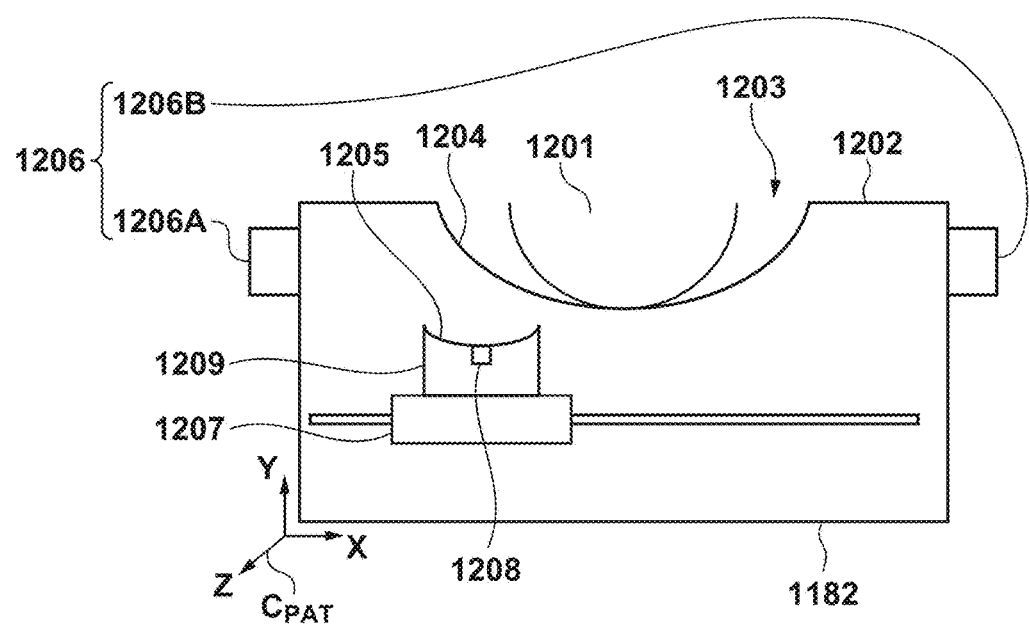
FIG. 12 is a schematic diagram showing a situation in which imaging is performed by a second medical imaging apparatus according to the third embodiment.

The second medical imaging apparatus 1182 is a photoacoustic tomography imaging apparatus (PAT apparatus), and obtains a PAT image (second image) by imaging a breast of an examinee in a second shape state (a state in which the breast is pressurized by the holding film) through irradiation with near infrared ray pulses within a range of an imaging region set by a later-described imaging region setting unit 108 of the image processing apparatus 1100. FIG. 12 is a schematic diagram showing a situation in which imaging is performed by the second medical imaging apparatus 1182. The examinee takes a prone position on a bed on an upper surface 1202 of the second medical imaging apparatus 1182. An object, that is to say, a breast 1201 on one side is inserted into an opening 1203 of the upper surface 1202 of the second medical imaging apparatus 1182. At this time, in order for irradiation light in a direction from a nipple toward a pectoralis major to reach the internal parts of the breast, the breast is held in a state where it is pressurized by a transparent holding film 1204 in a direction from the nipple to the pectoralis major, and imaged in a state where the thickness thereof is reduced. Here, the holding film 1204 has a certain tension force, and has a planar shape before the breast 1201 is inserted. The holding film 1204 is placed in a deformed and warped state by the inserted breast 1201 applying pressure thereto. That is to say, in the present embodiment, a surface that comes into contact with the breast (a holding surface) is a curved surface.

The second medical imaging apparatus 1182 includes an imaging unit 1209 made up of an irradiation unit 1208 and an ultrasound probe 1205. The imaging unit 1209 is attached to a movable stage 1207 so as to image parts thereabove (from a viewpoint of the imaging unit 1209, a direction orthogonal to the upper surface 1202). The irradiation unit 1208 irradiates the object with near infrared ray pulses, which represent irradiation light. The ultrasound probe 1205 receives photoacoustic signals generated inside the object in response to irradiation of the near infrared ray pulses. That is to say, the second medical imaging apparatus 1182 images the breast within a range of an imaging region while the movable stage 1207 is causing the imaging unit 1209 to move (scan) within the range of the imaging region. In the present embodiment, a PAT apparatus coordinate system C_PAT is defined as follows. A plane parallel to the upper surface 1202 is an XZ-plane, an axis representing a direction from the right hand to the left hand of the examinee is an X-axis, and an axis representing a direction from the feet to the head of the examinee is a Z-axis. Also, a normal direction of the upper surface 1202 is a Y-axis, and a direction from the anterior side to the posterior side of the examinee is a positive direction along the Y-axis. In addition, a lower end position on the right-hand side of the upper surface 1202 is the origin.

Figure 14:
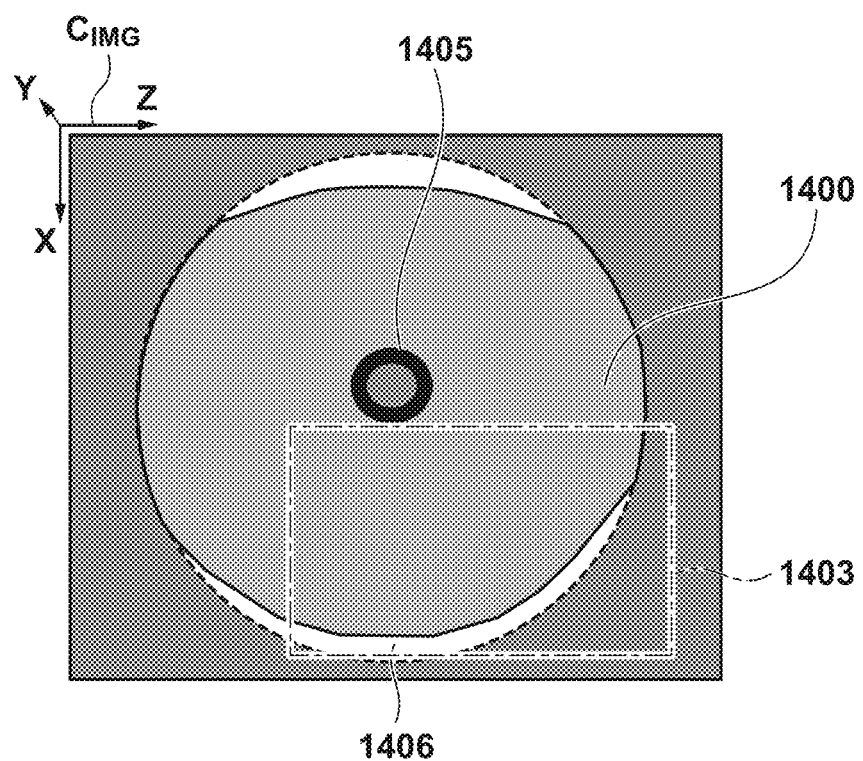
FIG. 14 is a schematic diagram showing an appearance image of a breast captured by a camera from a front side of an examinee in the third embodiment.

Also, a non-illustrated camera for capturing an appearance image (a third image) of the breast is mounted on the second medical imaging apparatus 1182. This camera is placed in a position in which the appearance of the breast can be imaged through the holding film 1204 from a front side of the examinee. C_CAM denotes a camera coordinate system in which a position of a focal point of the camera is the origin. It is assumed here that the camera has already been calibrated in the PAT apparatus coordinate system C_PAT. FIG. 14 is a schematic diagram showing an appearance image 1400 of the breast captured by the camera from the front side of the examinee. It is assumed that, in the present embodiment, the appearance image 1400 lies on an XZ-plane at Y=0.

<Configurations of Functional Blocks of Image Processing Apparatus 1100>

The image processing apparatus 1100 is connected to the data server 190, the second medical imaging apparatus 1182, the display unit 184, and the operation unit 186. The image processing apparatus 1100 includes a medical image obtaining unit 102, an appearance image obtaining unit 104, a deformation information obtaining unit 1106, an imaging region setting unit 108, a corresponding region calculation unit 110, an adjustment determination unit 111, a display image generation unit 112, an end determination unit 113, a region of interest setting unit 114, and a conversion region calculation unit 116.

The deformation information obtaining unit 1106 calculates and obtains deformation information by deforming and positioning an MRI image 200 with respect to the breast being pressurized by the holding film 1204, and outputs this deformation information to the corresponding region calculation unit 110.

<Processing Executed by Image Processing Apparatus 1100>

Figure 13:
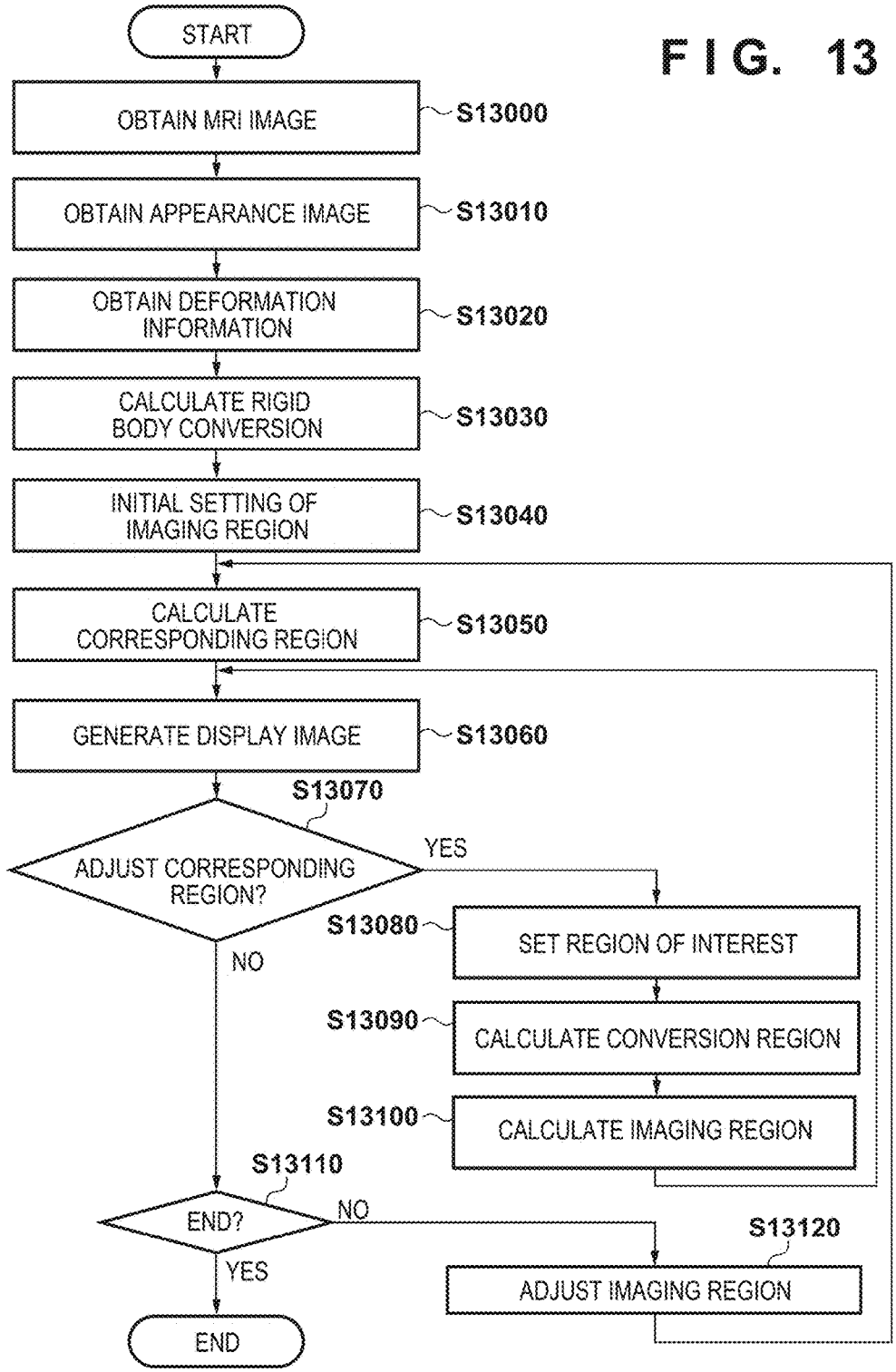
FIG. 13 is a flowchart showing a procedure of processing of the image processing apparatus according to the third embodiment.

Next, a description is given of a procedure of processing executed by the image processing apparatus 1100 according to the present embodiment with reference to a flowchart of FIG. 13. Compared to the processing executed by the image processing apparatus 100 according to the first embodiment, which has been described with reference to FIG. 5, processes of step S13020, step S13040, step S13100, and step S13120 according to the present embodiment differ from the corresponding processes of step S5020, step S5040, step S5100, and step S5120.

In step S13020, the deformation information obtaining unit 1106 obtains deformation information for deforming the MRI image into the shape of the breast being pressurized by the holding film 1204. The processing executed by the image processing apparatus 1100 according to the present embodiment is on the premise that the posture of the examinee in the PAT image coordinate system C_PAT substantially matches the posture of the examinee in an MRI image coordinate system C_MRI. That is to say, it is assumed that the breast is compressed by the holding film 1204 substantially along a Y-axis direction of the MRI image coordinate system C_MRI. It is also assumed that the external shape of the breast 1201 and the shape of a pectoralis major in the MRI image 200 are input at the time of a physical deformation simulation.

Here, the external shape of the breast 1201 in the PAT apparatus coordinate system C_PAT can be obtained using, for example, one or more ranging apparatuses 1206 that are placed in a position in which the breast on the second medical imaging apparatus 1182 can be measured (in the example of FIG. 12, ranging apparatuses 1206A, 1206B). That is to say, the external shape of the breast 1201 can be obtained by a user manually designating a breast region in range images of the breast captured by the ranging apparatuses 1206 using a non-illustrated mouse, keyboard, and the like. It is assumed that, at this time, the ranging apparatuses 1206 have already been calibrated in the PAT apparatus coordinate system C_PAT. Here, a nipple position in the PAT apparatus coordinate system C_PAT can also be obtained using the ranging apparatuses 1206. It should be noted that, in place of the external shape of the breast 1201, the shape of the holding film 1204 may be obtained and used with the use of the ranging apparatuses 1206.

Also, the shape of the pectoralis major in the MRI image coordinate system C_MRI can be obtained by applying a known image analysis method or the user's manual designation using the non-illustrated mouse, keyboard, and the like with respect to the MRI image 200.

In step S13040, the imaging region setting unit 108 configures initial setting of an imaging region of the second medical imaging apparatus 182. It is assumed that, in the present embodiment, an imaging region 1403 is set in an appearance image coordinate system C_IMG as shown in FIG. 14. Then, based on an initial value of the imaging region in the appearance image coordinate system C_IMG, an imaging region in the PAT apparatus coordinate system C_PAT is obtained. For example, four vertices of the set imaging region are first converted into four points in the camera coordinate system C_CAM, four intersections between the upper surface 1202 and four straight lines connecting these four points and the origin of the camera coordinate system are obtained, and the four intersections are converted into four points in the PAT apparatus coordinate system C_PAT. Then, a rectangle circumscribing these four points is regarded as an imaging region in the PAT apparatus coordinate system C_PAT.

In step S13100, based on a conversion region calculated in step S11090, the imaging region setting unit 108 calculates an imaging region of a PAT image captured by the second medical imaging apparatus 1182. Specifically, a cuboid circumscribing the conversion region calculated in step S11090 is calculated, and this cuboid is newly regarded as a three-dimensional imaging region. It is assumed that line segments of the cuboid are parallel to corresponding axes of the PAT apparatus coordinate system C_PAT.

In step S13120, based on an operation on the operation unit 186, the imaging region setting unit 108 adjusts the imaging region of the PAT image captured by the second medical imaging apparatus 1182. Specifically, the appearance image 1400 is displayed on the display unit 184, and the user manually adjusts a range of the set imaging region 1403 (two-dimensional rectangular region) on the displayed image using the non-illustrated mouse, keyboard, and the like. Furthermore, based on the imaging region in the appearance image coordinate system C_IMG, an imaging region in the PAT apparatus coordinate system C_PAT is obtained through a process similar to step S13040. For example, four vertices of the imaging region are converted into four points in the camera coordinate system C_CAM, four intersections between the upper surface 1202 and four straight lines connecting these four points and the origin of the camera coordinate system are obtained, and the four intersections are converted into four points in the PAT apparatus coordinate system C_PAT. Then, a rectangle circumscribing these four points is set as the imaging region in the PAT apparatus coordinate system C_PAT. Here, a cuboid region formed by pushing an imaging region (a rectangular region) on a two-dimensional plane at Y=0 in the PAT apparatus coordinate system C_PAT from Y=0 to Y=d (the distance from the upper surface 1202 to the deepest portion of the holding film 1204) is set as the three-dimensional imaging region.

As described above, the image processing apparatus 1100 according to the present embodiment includes a first image obtaining unit (the medical image obtaining unit 102) that obtains a first image (the MRI image 200) of an object (e.g., a breast) in a first shape state (an unheld state), the imaging region setting unit 108 that sets an imaging region of the object in a second shape state (a held state in which the object is held by the holding film 1204), the deformation information obtaining unit 1106 that obtains deformation information (a deformation function) indicating deformation of the object from the second shape state (the held state) to the first shape state (the unheld state), the corresponding region calculation unit 110 that calculates a corresponding region in the first shape state (the unheld state) corresponding to the imaging region based on the deformation information (the deformation function), and the display image generation unit 112 that generates a display image (an MRI_VR image, an MIP image) based on the first image (the MRI image 200) and the corresponding region.

In this way, when setting an imaging region of a PAT image, a corresponding region that corresponds to this imaging region can be displayed on an MRI image of the object, thereby allowing for visualization of a range to be imaged out of a reference image, such as an MRI image. Therefore, the user can adjust the imaging region while confirming the display. The present embodiment also allows for reduction in the burden of the examinee compared to a configuration in which a breast is pressurized from both sides.

First Modification Example of Third Embodiment

While the present embodiment has described an exemplary case in which an object is held by one holding film in such a manner that the object is pressurized and thus thinned, embodiments of the present invention are not limited in this way. For example, a breast may be held in a thinned state by placing the breast in an arch-shaped or bowl-shaped container (holding container) serving as a holding member. If the shape of the holding container is known, it is sufficient to estimate deformation of an MRI image such that the shape of the object in the MRI image matches the shape of the holding container. On the other hand, if the shape of the holding container is unknown, or if there is a matching agent or a matching liquid between the holding container and the object, deformation of the MRI image may be estimated in accordance with the external shape of a side surface of the breast obtained by a ranging apparatus. Also, the breast may be held by a planar holding plate pressed thereagainst from a direction of a nipple. In this case, a combination of the external shape of a side surface of the breast obtained by a ranging apparatus and the planar shape of the breast may be used as the external shape of the breast.

Second Modification Example of Third Embodiment

While the present embodiment has described an exemplary case in which the imaging region 1403 is a two-dimensional rectangular region, embodiments of the present invention are not limited in this way. For example, the imaging region 1403 may be a region enclosed by a circle or an ellipse depending on a method in which the movable stage 1207 causes the imaging unit 1209 to move (scan). Alternatively, it may be a region enclosed by any closed curve.

The present invention makes it possible to set an imaging region such that a region of attention inside an object can be imaged appropriately.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-006215, filed Jan. 16, 2014 and 2014-230105, filed Nov. 12, 2014 which are hereby incorporated by reference herein in their entirety.

The invention claimed is:

1. An image processing apparatus comprising at least one processor and memory coupled to each other and cooperating to act as:
   a first image obtaining unit configured to obtain a first medical image of an object in a first shape state;
   an imaging region setting unit configured to set a region to be imaged of the object in a second shape state, before taking a second medical image of the object in the second shape state;
   a deformation information obtaining unit configured to obtain deformation information indicating deformation of the object from the second shape state to the first shape state;
   a corresponding region calculating unit configured to calculate a corresponding region that corresponds to the region to be imaged in the first shape state based on the deformation information;
   a display control unit configured to cause a display unit to display the first medical image and the corresponding region; and
   an imaging region outputting unit configured to output information of the region to be imaged to a medical imaging apparatus in order to take the second medical image by using the medical imaging apparatus based on the information of the region to be imaged.

2. The image processing apparatus according to claim 1, wherein the imaging region setting unit re-sets the region to be imaged by accepting input of the region to be imaged based on a user operation.

3. The image processing apparatus according to claim 2, wherein the corresponding region calculating unit re-calculates the corresponding region in accordance with the re-setting of the region to be imaged.

4. The image processing apparatus according to claim 3, wherein the display control unit causes the display unit to again display the first medical image on which the corresponding region is superimposed in accordance with the re-calculation of the corresponding region.

5. The image processing apparatus according to claim 1, wherein the deformation information obtaining unit further obtains information related to error in estimation of deformation of the object from the second shape state to the first shape state, and
   the corresponding region calculating unit calculates the corresponding region based on the deformation information and the information related to the error.

6. The image processing apparatus according to claim 1, wherein the display control unit causes the display unit to display the first medical image by generating a volume rendering image or a maximum value projection image of the first medical image inside the corresponding region.

7. The image processing apparatus according to claim 1, wherein the display control unit causes the display unit to display the first medical image by generating a volume rendering image or a maximum value projection image of the first medical image outside the corresponding region.

8. The image processing apparatus according to claim 1, wherein the at least one processor and memory further cooperate to act as:
   a region of interest setting unit configured to set a region of interest by adjusting the corresponding region; and
   a conversion region calculating unit configured to calculate a conversion region that corresponds to the region of interest in the second shape state by deforming the region of interest based on the deformation information, wherein
   the imaging region setting unit sets the region to be imaged of the object based on the conversion region.

9. The image processing apparatus according to claim 1, wherein the first medical image is an MRI image of the object.

10. The image processing apparatus according to claim 1, wherein the at least one processor and memory further cooperate to act as an appearance image obtaining unit configured to obtain an appearance image of the object in the second shape state, wherein
    the display control unit causes the display unit to display the region to be imaged by generating a display image by overlapping the region to be imaged over the appearance image.

11. The image processing apparatus according to claim 1, wherein the region to be imaged is a region for capturing the second medical image of the object.

12. The image processing apparatus according to claim 11, wherein the second medical image is a photoacoustic tomography image of the object.

13. A control method for an image processing apparatus, the control method comprising:

obtaining a first medical image of an object in a first shape state;

setting a region to be imaged of the object in a second shape state, before taking a second medical image of the object in the second shape state;

obtaining deformation information indicating deformation of the object from the second shape state to the first shape state;

calculating a corresponding region that corresponds to the region to be imaged in the first shape state based on the deformation information;

causing a display unit to display the first medical image and the corresponding region, and outputting information of the region to be imaged to a medical imaging apparatus in order to take the second medical image by using the medical imaging apparatus based on the information of the region to be imaged.

14. A non-transitory computer-readable storage medium storing a program for causing a computer to execute a control method for an image processing apparatus, the control method comprising:

obtaining a first medical image of an object in a first shape state;

setting a region to be imaged of the object in a second shape state, before taking a second medical image of the object in the second shape state;

obtaining deformation information indicating deformation of the object from the second shape state to the first shape state;

calculating a corresponding region that corresponds to the region to be imaged in the first shape state based on the deformation information;

causing a display unit to display the first medical image and the corresponding region; and outputting information of the region to be imaged to a medical imaging apparatus in order to take the second medical image by using the medical imaging apparatus based on the information of the region to be imaged.

* * * * *